United States Patent
Auclair et al.

(10) Patent No.: US 11,351,146 B2
(45) Date of Patent: Jun. 7, 2022

(54) TOPICAL COMPOSITIONS FOR THE TREATMENT OF CUTANEOUS LEISHMANIASIS

(71) Applicant: AC BIOSCIENCE SA, Ecublens (CH)

(72) Inventors: Christian Auclair, Saint Arnoult en Yvelines (FR); Esther Fellous, Paris (FR); Patrice Le Pape, Vertou (FR); Jorge E. Kalil-Filho, Sao Paulo SP (BR)

( * ) Notice: Subject to any disclaimer, the term of this patent is extended or adjusted under 35 U.S.C. 154(b) by 0 days.

(21) Appl. No.: 16/644,278

(22) PCT Filed: Sep. 3, 2018

(86) PCT No.: PCT/EP2018/073576
§ 371 (c)(1),
(2) Date: Mar. 4, 2020

(87) PCT Pub. No.: WO2019/043212
PCT Pub. Date: Mar. 7, 2019

(65) Prior Publication Data
US 2021/0059979 A1    Mar. 4, 2021

(30) Foreign Application Priority Data
Sep. 4, 2017 (EP) .................................... 17306143

(51) Int. Cl.
| | |
|---|---|
| *A61K 31/353* | (2006.01) |
| *A61P 31/00* | (2006.01) |
| *A61P 29/00* | (2006.01) |
| *A61K 9/00* | (2006.01) |
| *A61K 9/107* | (2006.01) |
| *A61K 31/045* | (2006.01) |
| *A61K 31/196* | (2006.01) |

(52) U.S. Cl.
CPC .......... *A61K 31/353* (2013.01); *A61K 9/0014* (2013.01); *A61K 9/107* (2013.01); *A61K 31/045* (2013.01); *A61K 31/196* (2013.01); *A61P 29/00* (2018.01); *A61P 31/00* (2018.01)

(58) Field of Classification Search
CPC .... A61K 31/353; A61K 9/0014; A61K 9/107; A61K 31/045; A61K 31/196; A61K 31/167; A61K 45/06; A61K 31/01; A61K 31/352; A61P 31/00; A61P 29/00; Y02A 50/30

USPC ........................................................ 514/456
See application file for complete search history.

(56) References Cited

U.S. PATENT DOCUMENTS

2005/0165068 A1* 7/2005 Lepape .................. A61P 33/02
514/352

FOREIGN PATENT DOCUMENTS

WO        03/063858 A2    8/2003

OTHER PUBLICATIONS

Corpas-López et al., "(-)-a-Bisabolol, a Promising Oral Compound for the Treatment of Visceral Leishmaniasis," Journal of Natural Products, vol. 78, pp. 1202-1207, Year 2015.
Corpas-López et al., "The Sesquiterpene (-)-a-bisabolol is Active Against the Causative Agents of Old World Cutaneous Leishmaniasis Through the Induction of Mitochondrial-dependent Apoptosis," Apoptosis, vol. 21, pp. 1071-1081, Year 2016.
Corpas-López et al., Topical Treatment of Leishmania Tropica Infection Using (-)-a-Bisabolol Ointment in a Hamster Model: Effectiveness and Safety Assessment, Journal of Natural Products, vol. 79, pp. 2403-2407, Year 2016.
Da Silva et al., "The Leishmanicidal Flavonols Quercetin and Quercitrin Target Leishmania (Leishmania) Amazonensis Arginase," Experimental Parisitology, vol. 130, pp. 183-188, Year 2012.
Gundampati et al., "Tryparedoxin Peroxidase of Leishmania Braziliensis: Homology Modeling and Inhibitory Effects of Flavonoids for Anti-Leishmanial Activity," Bioinformation, vol. 10, No. 6, pp. 353-357, Year 2014.
Hiam et al., "Microtubule Target for New Antileishmanial Drugs Based on Ethyl 3-haloacetamidobenzoates," Journal of Enzyme Inhibition and Medicinal Chemistry, vol. 21, No. 3, pp. 305-312, Year 2006.

* cited by examiner

*Primary Examiner* — Taylor V Oh
(74) *Attorney, Agent, or Firm* — Dinsmore & Shohl LLP; Weston R. Gould

(57) ABSTRACT

The present invention relates to a composition comprising a combination of a (halogenoacetamido)benzoate, a flavonol and a terpene, and, as example, relates to a composition comprising the combination of ethyl 3-(2-chloroacetamido) benzoate, dihydroquercetin and bisabolol.
Said composition is for use in the treatment of leishmaniasis, especially cutaneous or mucosal leishmaniasis, the composition being applied topically for concomitantly treating both parasitic infection and skin inflammation of the infected area induced by leishmaniasis.

14 Claims, No Drawings

TOPICAL COMPOSITIONS FOR THE TREATMENT OF CUTANEOUS LEISHMANIASIS

CROSS REFERENCE TO RELATED APPLICATIONS

This application is a U.S. National Stage of PCT/EP2018/073576 filed Sep. 3, 2018, which depends from and claims priority to European Application No: 17306143.3 filed Sep. 4, 2017.

FIELD OF THE INVENTION

The present invention relates to the treatment of leishmaniasis, especially cutaneous leishmaniasis. In particular, the present invention relates to a composition comprising an (halogenoacetamido)benzoate, a flavonol and a terpene for the use in the treatment of leishmaniasis, especially topical treatment of cutaneous leishmaniasis. The present invention also relates to a process of manufacturing said composition.

BACKGROUND OF THE INVENTION

Leishmaniasis

Leishmaniasis is a parasitic disease spread by the bite of infected sandflies. It is endemic in 88 countries throughout Africa, Asia, Europe, and North and South America. There are an estimated 12 million cases worldwide, with 1.5 to 2 million new cases each year.

Leishmaniasis is divided into four main clinical forms and is caused by parasitic protozoa of the genus *Leishmania*. There are over 20 species and subspecies that infect humans via the bite of sandflies of subfamily phlebotominae. The life cycle of *Leishmania* parasites begin when an infected fly bites and injects *Leishmania* infective promastigotes which are present in its proboscis directly in the skin of a host. These promastigotes are then phagocytosed by macrophages that transform into amastigotes and are able to divide. Upon maximum levels of amastigote divisions, the macrophages burst releasing more amastigotes that are again re-phagocytosed. When an uninfected fly bites an infected individual, it ingests the amastigotes and these transform into promastigotes and divide in the midgut of the fly. Finally, these promastigotes migrate to the proboscis and are now able to transmit the disease.

The clinical features of the disease depend on the causative species and can range from simple, self-healing skin sores as found in cutaneous leishmaniasis (CL), to severe, life-threatening diseases affecting the internal organs of the body such as visceral leishmaniasis (VL).

One of the most common forms of the disease is cutaneous leishmaniasis that occurs most commonly in Iran, Afghanistan, Syria, Saudi Arabia, Peru and Brazil. Cutaneous leishmaniasis is characterized by skin lesions such as sores, which typically develop within several weeks or months after exposure. However, in some patients, the sores first appear months or years after the infection, in a context of skin traumatism (e.g. skin wounds or surgery). The sores can change in size and appearance over time. They typically progress from small papules to nodular plaques, and often lead to open sores with a raised border and central crater (ulcer), which can be covered with scales or crust. The lesions are usually painless but can be painful, particularly if open sores become infected with bacteria. Satellite lesions, regional lymphadenopathy, and nodular lymphangitis can be noted. The sores usually heal eventually, even without treatment. However, they can last for months or years and typically result in scarring.

A potential concern applies to some of the *Leishmania* species in South and Central America, because some parasites can spread from the skin to the mucosal surfaces of the nose or mouth and cause sores therein. This form of leishmaniasis, mucosal leishmaniasis (ML), might not be noticed until years after the original skin sores appear to have healed. Although mucosal leishmaniasis is uncommon, it has occurred in travelers and expatriates whose cases of cutaneous leishmaniasis were not treated, or were inadequately treated. The initial clinical manifestations typically involve the nose (chronic stuffiness, bleeding, and inflamed mucosa or sores) and less often the mouth. In advanced cases, ulcerative destruction of the nose, mouth, and pharynx can be noted, such as perforation of the nasal septum.

Existing Treatments

Anti-parasitic pentavalent antimonials, such as sodium stibogluconate or meglumine antimoniate, are presently the basis for all treatment of leishmaniasis. Long courses of these drugs are often required. Pentavalent antimony is thought to work by inhibition of adenosine triphosphate synthesis. The antimonial agent specifically used in the United States is sodium stibogluconate (Pentostam). After 20 days of treatment with pentavalent antimonials, there is usually evidence of healing, but lesions may not be re-epithelialized completely. Healing is determined by a healed appearance at two months, no relapse at 12 months, and no subsequent mucosal disease. The response to a particular regimen may vary not only among *Leishmania* species but also for the same species in different geographic regions.

Pentavalent antimonials have a high incidence of side effects. Side effects include aching; arthralgia; fatigue; gastrointestinal upset; elevation of amylase, lipase, and liver enzyme levels; leukopenia; anemia; and electrocardiographic abnormalities.

There is general agreement to consider that the commonly available drugs for the treatment of leishmaniasis have severe side effects, high cost and low efficacy (Shukla et al., *Applied Biochemistry and Biotechnology*, 2010, Vol. 160, pp. 2208-2218). Accordingly, there is still a need for treatment of leishmaniasis, and more especially for treatment of cutaneous leishmaniasis. EP1469845 discloses derivatives of haloacetaminobenzoic acid for use in the treatment of parasitic diseases, in particular in the treatment of leishmaniasis by inhibiting the at least partially the polymerization of the tubulin of the parasite without inhibiting that of the host cell. Although said derivatives could be applied topically or orally, their action focuses on the parasite, and do not alleviate or treat the skin or mucous lesions resulting from the infection.

Consequently, there is a need to propose a therapeutic composition to fight both against parasite of leishmaniasis and skin or mucous lesions resulting from the infection, in particular by reducing the healing time of the lesions.

Moreover, there is also a need to propose a composition that could also be used for preventing or limiting the occurrence of such lesions.

The Applicant found that a novel composition comprising a combination of an antileihmaniasis drug in the series of (halogenoacetamido)benzoate, a flavonol and a terpene, preferably a monoterpene or a sesquiterpene, provides a potent leishmaniasis treatment which both reduce side effects and improve the comfort of the treated subject compared to prior art treatments.

The therapeutic action of the composition according to the invention comprises the following effects:
- killing the parasite, i.e. anti-leishmanial activity;
- reducing the risk of resistance of the parasite to the treatment;
- limitation of inflammation and/or local skin necrosis;
- limitation of dissemination of the parasite to other tissues;
- activation of the wound healing process; and/or
- antibacterial and antifungal activity, thereby reducing the risk of secondary infection.

More particularly the invention relates to compositions comprising as example of the antiparasitic molecule (halogenoacetamido)benzoate either ethyl 3-(2-chloroacetamido) benzoate or ethyl 3-(2-bromoacetamido) benzoate. The flavonol may be chosen among: quercetin, kaempferol, dihydroquercetin or dihydrokaempferol, or a mixture thereof. The third compound of the combination of the present invention is a terpene that may be chosen among: linalol, bisabolol, beta caryophyllene or a mixture thereof. This combination is advantageously for use in a method of treating leishmaniasis, preferably visceral leishmaniasis, cutaneous leishmaniasis or mucosal leishmaniasis, more preferably cutaneous and/or mucosal leishmaniasis, and the associated inflammation of the infected area, especially skin and/or mucous inflammation.

Therapeutic Strategy According to the Present Invention

The originality of the proposed therapeutic strategy is to fight against both parasites and skin inflammation resulting from the infection. The achievement of this main objective is the advantageous use of topical formulations comprising the combination of the three active molecules namely the ethyl 3-chloroacetamidobenzoate, the flavonol dihydroquercetin (DHQ) and the sesquiterpene α(-) bisabolol.

Targeting Leishmanial Strains

Anti-leishmanial activity will occur through the inhibition of two different pharmacological targets namely parasite tubulin and tryparedoxine peroxidase. This dual action is expected to increase the efficiency of the treatment and will limit the occurrence of resistance.

Targeting Parasite Tubulin by (3-(2-Chloroacetamido) Ethyl Benzoate) or Related Molecules The molecule (3-(2-chloroacetamido) ethyl benzoate) referred to as MF29 and related molecules are efficient against various leishmanial strains both in vitro and in vivo. The antileishmanial activity of MF 29 has been evaluated against *L. mexicana*, *L. infantum* and *L. major*. MF 29 displays a high effect on all promastigotes strains. MF 29 was found 400-fold more active than glucantime, a drug usually used as antileishmanial drug in human and that, on both promastigote and intracellular amastigote (Abdala et al. Journal of Enzyme Inhibition and medicinal chemistry, 2006, 21, 305).

Targeting the Parasite Tryparedoxine Peroxidase (TryP) by Dihydroquercetin or Related Molecules TryP is targeted by the flavonoid dihydroquercetin (DHQ). TryP is a parasite enzyme acting downstream of the trypanothione reductase and involved in the detoxification of hydrogen peroxide and organic peroxides. TryP inhibitory property of DHQ is assessed by molecular modeling experiments showing an efficient docking of DHQ within the TP catalytic site with a binding energy close to −7500 kJ mol-1 (See, R. K. Gundampati, Bioinformation, 2014; 10(6): 353-357). It should be noticed that this NADPH-dependent detoxification pathway, so called trypanothione peroxidase, is validated as pharmacological target since tryparedoxine reductase (TryR) is one of the known target of antimonial compounds (SbIII).

Targeting Innate Immune Response

This strategy is based on the concept developed by the inventor concerning the common molecular and cellular mechanisms involved in skin inflammation and toxicity from various origins and the accumulation of evidences indicating that the innate immune response following leishmanial infection controls the extent and severity of skin injury as well as the dissemination of the parasite leading to a visceral disease. Accordingly, it is strongly suggested that the inflammation, ulceration and sometimes large tissue destruction observed in cutaneous leishmaniasis is mainly due to a strong immune response characterized by a mobilization and activation of various cells of the innate immunity. Among those cells, neutrophils seem to play a major role through the production of reactive oxygen species and release of inflammatory cytokines. It has been observed that the parasite inoculation early induces rapid and massive recruitment of neutrophils to the site of inoculation, that may involve different host and/or parasite-derived factors such as interleukin (IL) IL-8, IL-17 and tumor necrosis factor (TNF). In human neutrophils, all phagosomes containing promastigotes fuse with myeloperoxidase (MPO)-containing primary granules. However, destruction of the parasites requires the additional fusion of tertiary and specific granules and most the engulfed parasites survive and contribute to the dissemination of the infection. Both infected and non-infected neutrophils contribute to the development of inflammation and skin necrosis and accordingly, neutrophils are considered as the prominent component of the inflammatory infiltrate in chronic cutaneous, diffuse cutaneous and muco-cutaneous lesions. It has been found that *L. braziliensis* infection was a potent trigger for neutrophil activation, oxidative burst, degranulation and the production of IL-22 and IL-10. It can be therefore assumed that inhibition of neutrophils activation can be beneficial for patients suffering from cutaneous leishmaniosis accompanied by a major inflammatory syndrome and ulceration.

The control of the immune response in the infected skin areas will be achieved by the inhibition of the neutrophil activation at two different level namely oxidative burst and degranulation. This effect limits the development of inflammation, limits the local skin necrosis, limits the diffusion of promastigotes to macrophages and hence limits the dissemination of the parasite to other tissues.

The two molecules included in the composition of the present invention intended for the inhibition of neutrophil activation are flavonol, such as dihydroquercetin and terpenes such as alpha bisabolol:

In particular:

Dihydroquercetin inhibits neutrophils oxidative burst:

Neutrophils oxidative burst mainly result from the activation of NADPH oxidase which generate the reactive oxygen species (ROS) superoxide anion.

Alpha-bisabolol inhibits neutrophils migration and degranulation:

Alpha-Bisabolol is an inflammatory-inhibiting sesquiterpene (6-methyl-2-(4-methyl-3-cyclohexen-1-yl)-5-hepten-2-ol; 1-methyl-4-(1,5-dimethyl-1-hydroxyhex-4(5)-nyl)cyclohexen-1) which is found in various plants, including the herbal tea, chamomile, is mainly used in cosmetics and personal care products. The most important known effects of bisabolol are anti-inflammatory, wound-healing, anti-bacterial, anti-mycotic, anti-phlogistic. In addition, alpha-Bisabolol is used to increase diffusivity across the modified skin barrier and therefore to enhance transepidermal drug penetration.

Definitions

In the present invention, the following terms have the following meaning:

"subject" refers to a mammal, preferably a human. In one embodiment, a subject may be a "patient", i.e. a warm-blooded animal, more preferably a human, who/which is awaiting the receipt of, or is receiving medical care or was/is/will be the object of a medical procedure, or is monitored for the development of leishmaniasis. In one embodiment, the subject is an adult (for example a subject above the age of 18). In another embodiment, the subject is a child (for example a subject below the age of 18). In one embodiment, the subject is a male. In another embodiment, the subject is a female.

"treating" or "treatment" refers to both therapeutic treatment and prophylactic or preventative measures; wherein the object is to prevent or slow down or alleviate leishmaniasis related symptoms. Those in need of treatment include those already with leishmaniasis as well as those prone to have leishmaniasis or those in whom leishmaniasis is to be prevented. A subject or mammal is successfully "treated" for leishmaniasis if, after receiving a therapeutic amount of a composition for use according to the present invention, the patient shows observable and/or measurable reduction in or absence of one or more of the following: reduction in the number of pathogenic parasites; reduction in the percent of total parasites that are pathogenic; and/or relief to some extent, of one or more of the symptoms associated with leishmaniasis (including, without limitation, skin or mucosal lesions such as open or closed sores); reduced morbidity and mortality, and improvement in quality of life issues. The above parameters are readily measurable by routine procedures familiar to a physician.

"therapeutically effective amount" means the level or amount of the composition of the invention that is aimed at, without causing significant negative or adverse side effects to the target, (1) delaying or preventing the onset of leishmaniasis; (2) slowing down or stopping the progression, aggravation, or deterioration of one or more symptoms of leishmaniasis; (3) bringing about ameliorations of the symptoms of leishmaniasis or alleviating the symptoms of leishmaniasis; or (4) reducing the severity or incidence of leishmaniasis symptoms. A therapeutically effective amount may be administered prior to the onset of leishmaniasis, for a prophylactic or preventive action. Alternatively, or additionally, the therapeutically effective amount may be administered after initiation of leishmaniasis symptoms, for a therapeutic action or maintenance of a therapeutic action.

"therapeutic composition" refers to a composition, having the capacity, when administered in a suitable amount, of slowing down or stopping the progression, aggravation, or deterioration of one or more symptoms of leishmaniasis or of alleviating the symptoms of leishmaniasis.

"pharmaceutic composition" refers to a composition comprising an active principle in association with a pharmaceutically acceptable vehicle. A pharmaceutical composition is for therapeutic use, and relates to health. Especially, a pharmaceutical composition may be indicated for treating leishmaniasis.

"pharmaceutically acceptable" refers to a component that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, injected preparations should meet sterility, pyrogenicity, general safety and purity standards as required by regulatory offices, such as, for example, FDA Office or EMA.

"about" preceding a figure means more or less 10% of the value of said figure.

In one embodiment, a cosmetic composition of the invention aims at reducing or preventing the appearance of the visible cutaneous or mucosal signs of leishmaniasis, thereby maintaining the skin or mucosa in good condition and/or or modify their aspects.

"vehicle" refers to a substance with which the component of interest is mixed or wherein the component of interest is dissolved.

DETAILED DESCRIPTION

Composition

In a first aspect the present invention relates to a composition comprising a combination of a (halogenoacetamido)benzoate, a flavonol and a terpene, and, as example, relates to a composition comprising the combination of ethyl 3-(2-chloroacetamido)benzoate, dihydroquercetin and bisabolol. Ethyl 3-(2-chloroacetamido)benzoate (ECAB), also known as 3-(2-chloroacetylamino)benzoic acid ethyl ester, or ethyl 3-(chloroacetyl)aminobenzoate (CAS number [58915-19-8]), is a compound of formula (I):

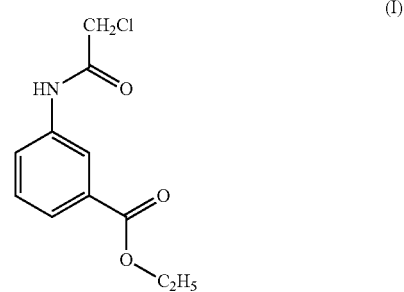

In one embodiment, the concentration of the (halogenoacetamido)benzoate, for instance ECAB, in the composition according to the invention ranges from 0.01% to 2.0% w/w (i.e. in weight, by weight of the total composition), preferably from 0.1% to 1% w/w, more preferably from 0.3% to 0.7% w/w.

Dihydroquercetin (DHQ) is the common name of 3,3',4',5,7-pentahydroxyflavone dehydrate, also called 2-(3,4-dihydroxyphenyl)-3,5,7-trihydroxy-4H-1-benzopyran-4-one dehydrate, also known as taxifolin (CAS number [480-18-2]).

In one embodiment, DHQ is extracted from a type of larch wood, preferably from Siberian larch. In an embodiment, DHQ containing powder contains at least 96% w/w by weight of DHQ and corresponds to the technical requirements and sanitary rules on the basis of analytical and microbiological reports.

In one embodiment of the present invention, the concentration of the flavonol, for instance DHQ, in the composition according to the invention ranges from 0.05% to 10% w/w (i.e. in weight, by weight of the total composition), preferably from 0.1% to 5.0% w/w, more preferably from 0.2% to 3%. In a specific example DHQ may be present at a concentration from 1.0% to 2.0% w/w.

Bisabolol is the common name of 6-methyl-2-(4-methyl-3-cyclohexen-1-yl)-5-hepten-2-ol, or 1-methyl-4-(1,5-dimethyl-1-hydroxyhex-4(5)-nyl)cyclohexen-1, also known as levomenol (CAS number [23089-26-1]). Bisabolol is a sesquiterperne found in various plants, including herbal tea and chamomile.

In one embodiment, the concentration of the terpene, for instance bisabolol, in the composition according to the invention ranges from 0.01% to 3.0% w/w (i.e. in weight, by weight of the total composition), preferably ranges from 0.05% to 2.5% w/w, more preferably from 0.05% to 2.0% w/w, even more preferably from 0.1% to 2.0% w/w.

In one embodiment, the composition according to the invention comprises or consists of ECAB, DHQ and bisabolol, in association with any acceptable vehicle. According to one embodiment, the composition according to the invention comprises ECAB, DHQ and bisabolol, in association with a pharmaceutically acceptable vehicle.

In one embodiment, the composition according to the invention comprises:
from 0.01% to 2.0% w/w of ECAB, preferably from 0.05% to 1% w/w, more preferably from 0.1% to 0.7% w/w, and
from 0.05% to 10% w/w of DHQ, preferably from 0.1% to 5.0% w/w, more preferably from 0.2% to 3.0% w/w, and
from 0.01% to 3.0% w/w of bisabolol, preferably from 0.05% to 2.5% w/w, more preferably from 0.05% to 2.0% w/w, even more preferably from 0.1% to 2.0% w/w,
and a pharmaceutically or cosmetically acceptable vehicle.

In one embodiment, the composition according to the invention further comprises at least one compound selected from the group comprising animal fat, vegetable fat, higher alcohols, such as fatty alcohols, glycols, mineral oil or a mixture thereof. In one embodiment, the composition according to the invention comprises an acceptable vehicle which comprises at least one compound selected from the group comprising animal fat, vegetable fat, higher alcohols, glycols, mineral oil or a mixture thereof.

A non-limitative example of animal fat is stearic acid. Examples of vegetable fat include, but are not limited to linoleic acid, jojoba oil (also called oil *Simmondsia chinensis*), sweet almond oil, avocado oil or a mixture thereof. Fatty alcohols are preferably with more than 10 carbon atoms, more preferably more than 12 carbon atoms, examples include, but are not limited to cetearyl alcohol, stearyl alcohol, cetylic alcohol. Examples of glycols include, but are not limited to propylene glycol. Examples of mineral oil include, but are not limited to paraffin oil.

In one embodiment, the composition according to the invention further comprises at least one component selected from the group comprising surfactants, pigments, stabilizers, emollients, humectants or a mixture thereof.

Examples of surfactants include, but are not limited to PEG-100 stearate, PEG-20 stearate or a mixture thereof. Examples of stabilizers include, but are not limited to carbomer. Examples of pigments include, but are not limited to zinc oxide. Examples of emollients include, but are not limited to caprylic/capric triglyceride, dicapryl ether, glyceryl stearate, glyceryl monostearate or a mixture thereof. Examples of humectants include, but are not limited to glycerin, sorbitol or a mixture thereof.

In one embodiment, the composition according to the invention further comprises perfume, such as for example citronellol, geraniol, limonene, cinnamyl alcohol, butyl phenyl methylpropional, or a mixture thereof.

In one embodiment, the composition according to the invention further comprises preservatives such as, for example, imidazolidinyl urea.

In one embodiment, the composition according to the invention further comprises water.

In one embodiment, the composition according to the invention is designed for topical administration. In one embodiment, the composition according to the invention is in a form adapted to topical administration, such as, for example, in the form of a cream, a gel, an ointment, a solution, an emulsion, a mask, a milk, a lotion, a serum, a paste, a stick, a foam or a suspension. In a preferred embodiment, the composition according to the invention is a cream or a stick. In another preferred embodiment, the composition according to the invention is a gel. In a further preferred embodiment, the composition according to the invention is an oil-in-water emulsion.

In an embodiment, the composition according to the invention is a therapeutic composition. In one embodiment, the composition according to the invention is a pharmaceutical composition.

Treatment of Leishmaniasis

In a second aspect, this invention relates to a composition comprising a combination of a (halogenoacetamido)benzoate, a flavonol and a terpene, preferably comprising ethyl 3-(2-chloroacetamido)benzoate, dihydroquercetin and bisabolol for use in the treatment of leishmaniasis, preferably visceral leishmaniasis, cutaneous leishmaniasis or mucosal leishmaniasis, more preferably cutaneous leishmaniasis or mucosal leishmaniasis, and the associated inflammation of the infected area.

The term "treatment of leishmaniasis" comprises treating the inflammation in the infected areas due to, or associated with, leishmaniasis. By "infected areas" is meant any part of the body where inflammation caused by leishmaniasis is present. Examples of such infected areas are, without limitation, skin and mucosa.

In a third aspect, the invention relates to a method of treating a subject suffering from leishmaniasis by administering an effective amount of a composition comprising ethyl 3-(2-chloroacetamido)benzoate (ECAB), dihydroquercetin (DHQ) and bisabolol or any composition comprising a (halogenoacetamido)benzoate, a flavonol and a terpene to a subject in need thereof.

In a fourth aspect, the invention relates to the use of a composition comprising ethyl 3-(2-chloroacetamido)benzoate (ECAB), dihydroquercetin (DHQ) and bisabolol or any composition comprising a (halogenoacetamido)benzoate, a flavonol and a terpene in the manufacture of a medicament for the treatment of leishmaniasis.

In one embodiment, the leishmaniasis is visceral leishmaniasis, cutaneous leishmaniasis or mucosal leishmaniasis. In a particular embodiment, the leishmaniasis is cutaneous leishmaniasis.

In one embodiment, the subject is infected by *Leishmania aethiopica, Leishmania amazonensis, Leishmania braziliensis, Leishmania donovani, Leishmania guyanensis, Leishmania infantum, Leishmania lainsoni, Leishmania lindenbergi, Leishmania mexicana, Leishmania major, Leishmania naiffi, Leishmania panamensis, Leishmania peruviana, Leishmania shawi, Leishmania tropica* and/or *Leishmania*

*venezuelensis*. In a particular embodiment, the subject is infected by *Leishmania amazonensis, Leishmania donovani,* and/or *Leishmania major.*

In one embodiment, leishmaniasis related symptoms is an inflammation induced by leishmaniasis parasite infection in skin or mucosa.

In one embodiment, treating leishmaniasis means preventing and/or reducing visible signs of leishmaniasis. The term "visible signs of leishmaniasis" includes but is not limited to skin or mucosal lesions such as papules, nodular plaques and open or closed sores.

In one embodiment, treating leishmaniasis means preventing and/or limiting cutaneous or mucosal discomfort induced by leishmaniasis. Examples of discomfort induced by leishmaniasis include, but are not limited to, itching and pain.

In an embodiment, the composition used in the treatment according to the invention is a therapeutic composition. In one embodiment, the composition used in the treatment according to the invention is a pharmaceutical composition.

In one embodiment, the composition used in the treatment according to the invention is for external use. In one embodiment, the composition is for topical application, preferably for use in the treatment of cutaneous leishmaniasis or mucosal leishmaniasis. In an embodiment, the treatment according to the invention requires the composition to be applied on inflamed skin or mucosa.

In one embodiment, an amount of composition used in the treatment according to the invention is applied which is sufficient to cover the afflicted area of the skin or mucosa with a thin layer of the composition.

In one embodiment, the composition used in the treatment according to the invention may be applied one, two, three or more times a day. In one embodiment, the composition used in the treatment according to the invention may be applied during 7, 14 or 21 days or until the visible symptoms of leishmaniasis disappear.

Device and Kit

In a fifth aspect, the invention relates to a device including a composition comprising ethyl 3-(2-chloroacetamido)benzoate (ECAB), dihydroquercetin (DHQ) and bisabolol or any composition comprising a (halogenoacetamido)benzoate, a flavonol and a terpene according to the invention.

In one embodiment, the device is a delivery device. In one embodiment, the device is a medical device.

In a sixth aspect, the invention relates to a kit comprising the composition a composition comprising ethyl 3-(2-chloroacetamido)benzoate (ECAB), dihydroquercetin (DHQ) and bisabolol or any composition comprising a (halogenoacetamido)benzoate, a flavonol and a terpene according to the invention, and/or a device comprising the composition according to the invention.

Process of Manufacture

In a seventh aspect, the invention relates to a process for manufacturing the composition according to the invention. In an embodiment, the process of the invention comprises a step of blending ECAB, DHQ and bisabolol or any composition comprising a (halogenoacetamido)benzoate, a flavonol and a terpene, with an acceptable vehicle. In one embodiment, the process of the invention comprises a preliminary step of dissolving DHQ or any flavonol in jojoba oil (*Simmondsia chinensis*) or sweet almond oil before blending the three active components with an acceptable vehicle.

Examples

The present invention is further illustrated by the following examples.

Compositions According to the Invention

Examples of compositions comprising ECAB, DHQ, bisabolol and a pharmaceutically acceptable vehicle being an oil/water emulsion are presented in the table 1 below.

TABLE 1

| Composition example | ECAB (% w/w) | DHQ (% w/w) | bisabolol (% w/w) | [Vehicle] |
| --- | --- | --- | --- | --- |
| 1 | 0.3 | 0.2 | 0.1 | qsp 100% |
| 2 | 0.4 | 0.5 | 0.5 | qsp 100% |
| 3 | 0.5 | 1.0 | 1.0 | qsp 100% |
| 4 | 0.6 | 2.0 | 1.5 | qsp 100% |
| 5 | 0.7 | 3.0 | 2.0 | Qsp 100% |
| 6 | 1.0 | 5.0 | 3.0 | Qsp 100% |

From the knowledge of the inventor, it is the first time that a topical formulation targeting both the parasite and the cells responsible for the inappropriate immune response is proposed for the treatment of cutaneous leishmaniasis.

A trial is being performed on dogs having leishmaniasis.

Infected dogs have been treated by topical formulation of example 6 in the form of a cream containing, as active ingredients, ethyl 3-(2 chloroacetamido)benzoate (1% w/w), dihydroquercetin 5% w/w) and bisabolol (3% w/w).

Preliminary data coming from this going on trial in dogs having leishmaniasis show an objective response in the treated dog population as evidenced by a significant reduction of the size of the cutaneous lesions.

The invention claimed is:

1. A composition comprising a combination of a (halogenoacetamido)benzoate, a flavonol and a terpene, wherein
   the (halogenoacetamido)benzoate is ethyl 3-(2-chloroacetamido)benzoate or ethyl 3-(2-bromooacetamido)benzoate,
   the flavonol is selected from the group consisting of quercetin, kaempferol, dihydroquercetin, dihydrokaempferol, and mixture thereof,
   the terpene is selected from the group consisting of linanol, bisabolol, beta caryophyllene and a mixture thereof.

2. The composition according to claim 1, wherein the concentration of the (halogenoacetamido)benzoate ranges from 0.01% to 2% in weight of the total weight of the composition (w/w).

3. The composition according to claim 1, wherein the concentration of the flavonol ranges from 0.05% to 10% in weight of the total weight of the composition (w/w).

4. The composition according to claim 1, wherein the concentration of the terpene ranges from 0.01% to 3.0% in weight of the total weight of the composition (w/w).

5. The composition according claim 1, comprising ethyl 3-(2 chloroacetamido)benzoate, dihydroquercetin, bisabolol, and a pharmaceutically acceptable vehicle.

6. The composition according to claim 5, comprising from 0.1% to 0.7% w/w ethyl 3-(2-chloroacetamido)benzoate, from 0.2% to 3% w/w dihydroquercetin, from 0.1% to 0.5% w/w bisabolol, and the pharmaceutically acceptable vehicle.

7. The composition according claim 1, wherein the composition further comprises at least one of animal fat, vegetable fat, fatty alcohols, glycols or mixtures thereof.

8. The composition according to claim 1, wherein the composition further comprises at least one surfactant, pigment, stabilizer, emollient, humectant, or mixtures thereof.

9. The composition according to claim 1, wherein the composition is a cream, a gel, an ointment, a solution, an emulsion, an oil-in-water emulsion, a mask, a stick, a milk, a lotion, a serum, a paste, a foam, or a suspension.

10. The composition of claim 1 wherein the terpene is a monoterpene or a sesquiterpene.

11. A method for the treatment of leishmaniasis and any, leishmaniasis associated inflammation of an infected area, comprising administering to a subject in need thereof the composition of claim 1.

12. The method of claim 11, wherein the composition is for topical application, and the leishmaniasis is cutaneous leishmaniasis or mucosal leishmaniasis.

13. A delivery device comprising the composition according to claim 1.

14. A process of manufacturing the composition according to claim 1 comprising a step of blending a (halogenoacetamido)benzoate, a flavonol and a terpene with a pharmaceutical acceptable vehicle.

* * * * *